United States Patent
Lesieur et al.

(10) Patent No.: US 8,549,897 B2
(45) Date of Patent: Oct. 8, 2013

(54) SYSTEM AND METHOD FOR SCREENING LIQUID COMPOSITIONS

(75) Inventors: Yves Lesieur, Le Havre (FR); Noel Lecuyer, Gournay en Caux (FR)

(73) Assignee: Chevron Oronite S.A. (FR)

(*) Notice: Subject to any disclaimer, the term of this patent is extended or adjusted under 35 U.S.C. 154(b) by 608 days.

(21) Appl. No.: 12/460,768

(22) Filed: Jul. 24, 2009

(65) Prior Publication Data

US 2011/0016954 A1   Jan. 27, 2011

(51) Int. Cl.
*G01N 33/30* (2006.01)

(52) U.S. Cl.
USPC .......................................... 73/54.05; 73/53.06

(58) Field of Classification Search
USPC ....................................................... 73/53.05
See application file for complete search history.

(56) References Cited

U.S. PATENT DOCUMENTS

| | | | |
|---|---|---|---|
| 3,059,467 A * | 10/1962 | Meguerian et al. | 73/61.62 |
| 3,108,468 A * | 10/1963 | Mickel | 73/61.62 |
| 3,200,638 A * | 8/1965 | De Haut | 73/53.05 |
| 3,438,757 A | 4/1969 | Honnen et al. | |
| 3,565,804 A | 2/1971 | Honnen et al. | |
| 3,574,576 A | 4/1971 | Honnen et al. | |
| 3,680,356 A * | 8/1972 | Felton, Jr. | 374/57 |
| 3,785,196 A * | 1/1974 | Smith | 73/53.05 |
| 3,848,056 A | 11/1974 | Fonseca et al. | |
| 3,960,515 A | 6/1976 | Honnen | |
| 4,031,023 A | 6/1977 | Mosser et al. | |
| 4,057,999 A * | 11/1977 | Bazika et al. | 73/53.06 |
| 4,160,648 A | 7/1979 | Lewis et al. | |
| 4,191,537 A | 3/1980 | Lewis et al. | |
| 4,197,409 A | 4/1980 | Lilburn | |
| 4,231,759 A | 11/1980 | Udelhofen et al. | |
| 4,233,168 A | 11/1980 | Lewis et al. | |
| 4,236,020 A | 11/1980 | Lewis et al. | |
| 4,243,798 A | 1/1981 | Franklin et al. | |
| 4,270,930 A | 6/1981 | Campbell et al. | |

(Continued)

FOREIGN PATENT DOCUMENTS

| | | |
|---|---|---|
| EP | 1 927 843 | 6/2008 |
| FR | 2 880 689 | 7/2006 |

(Continued)

OTHER PUBLICATIONS

International Search Report issued in Singapore Counterpart Application No. 201005276-9.

(Continued)

*Primary Examiner* — Hezron E Williams
*Assistant Examiner* — Mark A Shabman

(57) ABSTRACT

Disclosed herein is a system and method for screening a liquid composition. The system includes (a) a test cell having a top portion and a bottom portion, the test cell comprising (i) a test panel removably mounted to the top portion of the test cell at an angle of between about 10 to about 45 degrees to the horizontal of the test cell; (ii) a reservoir for holding the liquid composition; and (iii) a means for applying a substantially uniform coating of the liquid composition from the reservoir to at least a portion of the test panel; (b) a means for heating the test panel according to a first temperature control program; (c) a means for heating the reservoir according to a second temperature control program; and (d) a means for supplying an oxidizing gas to the test cell.

29 Claims, 7 Drawing Sheets

(56) References Cited

U.S. PATENT DOCUMENTS

| | | | |
|---|---|---|---|
| 4,288,612 A | 9/1981 | Lewis et al. | |
| 4,729,769 A | 3/1988 | Schlicht et al. | |
| 4,832,702 A | 5/1989 | Kummer et al. | |
| 4,849,178 A | 7/1989 | Azuma | |
| 4,854,159 A * | 8/1989 | Bates | 73/53.05 |
| 4,881,945 A | 11/1989 | Buckley, III | |
| 5,112,364 A | 5/1992 | Rath et al. | |
| 5,287,731 A | 2/1994 | Florkowski et al. | |
| 5,328,619 A | 7/1994 | Conary | |
| 5,393,309 A | 2/1995 | Cherpeck | |
| 5,569,842 A * | 10/1996 | Silvestri | 73/53.05 |
| 5,588,973 A | 12/1996 | Blackborow et al. | |
| 5,620,486 A | 4/1997 | Cherpeck | |
| 5,662,417 A * | 9/1997 | Tyus | 374/45 |
| 5,697,988 A | 12/1997 | Malfer et al. | |
| 5,916,825 A | 6/1999 | Cherpeck | |
| 5,954,843 A | 9/1999 | Cherpeck | |
| 5,993,497 A | 11/1999 | Cherpeck et al. | |
| 6,114,542 A | 9/2000 | Cherpeck | |
| 6,203,584 B1 | 3/2001 | Fuentes-Afflick et al. | |
| 6,217,624 B1 | 4/2001 | Morris et al. | |
| 6,365,413 B1 | 4/2002 | Hall et al. | |
| 6,372,696 B1 | 4/2002 | Tipton | |
| 6,616,776 B1 | 9/2003 | Ahmadi et al. | |
| 6,651,604 B2 | 11/2003 | Ahmadi et al. | |
| 6,652,667 B2 | 11/2003 | Ahmadi et al. | |
| 2008/0022757 A1 * | 1/2008 | Zhou et al. | 73/53.05 |
| 2008/0127717 A1 | 6/2008 | Lesieur | |
| 2008/0127718 A1 | 6/2008 | Lesieur | |

FOREIGN PATENT DOCUMENTS

| | | |
|---|---|---|
| FR | 2880689 | 7/2006 |
| GB | 1486144 | 9/1977 |
| GB | 2355125 | 2/2002 |

OTHER PUBLICATIONS

U.S. Appl. No. 10/402,170, filed Mar. 28, 2003, Thiel et al.
International Search Report issued in counterpart European Patent Application No. 10170597.

* cited by examiner

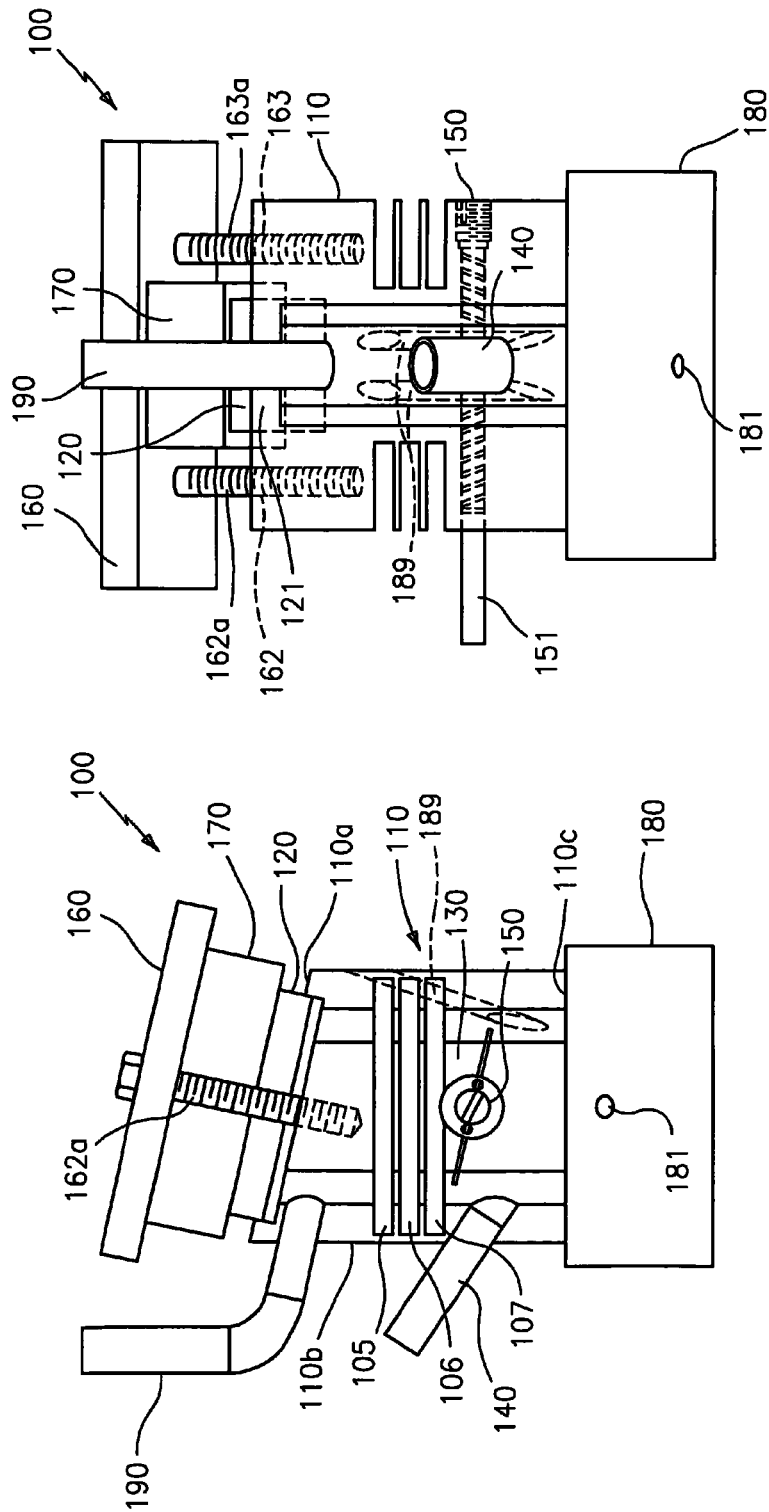

SYSTEM AND METHOD FOR SCREENING LIQUID COMPOSITIONS

BACKGROUND OF THE INVENTION

1. Technical Field

The present invention generally relates to a system and method for screening liquid compositions such as fuels and lubricating oil compositions.

2. Description of the Related Art

It is critical to the success of many companies that products can be efficiently sampled and screened. For example, in the case of a lubricating oil composition, the lubricating oils may be subjected to a demanding environment during use in an internal combustion engine. The environment results in the oil suffering oxidation which is catalyzed by the presence of impurity species in the oil such as, for example, iron compounds, and is also promoted by the elevated temperatures experienced by the oil during use. The catalyzed oxidation of the oil not only contributes to the formation of corrosive oxidation products and sludge in the oil but can also cause the viscosity of the oil to increase or even solidify.

In addition, deposits can adversely affect the operation of the engine. For example, deposits can form on the areas of an engine contacted by lubricating oil compositions. Deposits that form in high temperature areas of an engine can lead to mild engine damage such as piston and cylinder scuffing, leading to problems such as e.g. increased engine emissions. In extreme cases, such deposits can result in, e.g., valve sticking and ring sticking, leading to possible catastrophic damage of the engine. Deposits in low temperature areas of the engine such as the cranckcase typically take the form of sludge. Sludge formation can reduce the cooling efficiency of an engine, and in severe cases can impede the operation of pumps.

Areas of a fuel intake system can also be burdened by the formation of deposits. Typical areas include carburetor ports, the throttle body and venturies, engine intake valves, etc. For example, deposits on the carburetor throttle body and venturies increase the fuel to air ratio of the gas mixture to the combustion chamber thereby increasing the amount of unburned hydrocarbon and carbon monoxide discharged from the chamber. The high fuel-air ratio also reduces the gas mileage obtainable from the vehicle.

When deposits on the engine intake valves get sufficiently heavy, they can restrict the gas mixture flow into the combustion chamber. This restriction starves the engine of air and fuel and results in a loss of power. Deposits on the valves also increase the probability of valve failure due to burning and improper valve seating. In addition, these deposits may break off and enter the combustion chamber possibly resulting in mechanical damage to the piston, piston rings, engine head, etc.

The formation of these deposits can be inhibited as well as removed by incorporating an active detergent into, for example, the fuel. These detergents function to cleanse these deposit-prone areas of the harmful deposits, thereby enhancing engine performance and longevity.

Lubricating oil and lubricating oil additive suppliers as well as fuel and fuel additive suppliers are therefore constantly performing research to discover new materials that are improved in these aspects. In addition, there are several ASTM engine Sequence tests which must be run to achieve passing results in order to certify candidate engine lubricant formulations and fuel formulations that meet API (American Petroleum Institute) and ILSAC (International Lubricant Standardization and Approval Committee) standards. However, these tests are very expensive and time consuming.

As a result, bench test methods can be used to assess the performance of any new lubricating oil composition or fuel composition prior to it being recommended to a potential user. A good bench test is therefore a crucial component of new product development, quality control, i.e., fitness for use, and product improvement. For example, these bench tests are also a useful marketing tool in trying to convince a potential user to employ an existing lubricating oil composition or an existing user to employ an improved lubricating oil composition. They serve to demonstrate to a customer that a particular lubricating oil composition will perform effectively in their specific process. Therefore, it would be desirable to provide a laboratory bench test that can simulate the oxidation and detergency performance of a new lubricating oil composition or fuel composition under operating conditions.

One bench test that evaluates the oxidation and detergency tendency of a lubricating oil is the "panel coker" test, e.g., Federal Test Method Standard 791B-3462. In the panel coker test, approximately 100 g of oil is preheated in a sump and then intermittently projected by means of a rotating oil stirrer onto an aluminum test plate heated at a high temperature for a period of 48 hours. The amount of deposit on the aluminum plate is weighed at the end of the 48 hours.

Accordingly, there is a need for an improved system and method for screening liquid compositions such as lubricating oil compositions.

SUMMARY OF THE INVENTION

In accordance with one embodiment of the present invention, a system for screening a liquid composition is provided, the system comprising:

(a) a test cell having a top portion and a bottom portion, the test cell comprising (i) a test panel removably mounted to the top portion of the test cell at an angle of between about 10 to about 45 degrees to the horizontal of the test cell; (ii) a reservoir for holding the liquid composition; and (iii) a means for applying a substantially uniform coating of the liquid composition from the reservoir to at least a portion of the test panel;

(b) a means for heating the test panel according to a first temperature control program;

(c) a means for heating the reservoir according to a second temperature control program; and (d) a means for supplying an oxidizing gas to the test cell.

In accordance with a second embodiment of the present invention, a method for screening a liquid composition is provided, the method comprising:

(a) providing a test cell having a top portion and a bottom portion, the test cell comprising (i) a test panel removably mounted to a top portion of the test cell at an angle of between about 10 to about 45 degrees to the horizontal of the test cell; (ii) a reservoir for holding the lubricating oil composition; and (iii) a means for applying the liquid composition from the reservoir to the test panel;

(b) introducing the liquid composition into the reservoir of the test cell;

(c) heating the test panel according to a first temperature controlled program;

(d) heating the reservoir according to a second temperature controlled program, wherein the test panel is heated to a temperature greater than the temperature of the reservoir;

(e) introducing an oxidizing gas to the test cell;

(f) applying a substantially uniform coating of the liquid composition from the reservoir to at least a portion of the test panel; and (g) measuring the oxidation stability of the liquid composition.

The system and method of the present invention advantageously allow for a simple and inexpensive way to determine the properties of a liquid composition such as oxidative stability, detergency and viscosity. In addition, the system and method of the present invention allow (1) the use of a relatively small sample of a liquid composition, such as a few milliliters; (2) little to no consumption of the liquid composition; (3) a relatively short testing period; and (4) improved precision of test results. If desired, the method can be performed in a semi-automated manner and without highly skilled personnel. In addition, the system and method described herein are capable of providing a variation of several test parameters, allowing closer replication of real-world conditions such as are found in, e.g., automobile engines. Further, the system and method described herein can be configured such that online measurements of liquid composition properties such as the viscosity of the test sample may be measured during the operation of the test.

BRIEF DESCRIPTION OF THE DRAWINGS

Various embodiments are described below with reference to the drawings wherein:

FIG. 1 is a schematic diagram of a side view of one embodiment of a system according to the present invention;

FIG. 2 is a schematic diagram of a rear view of one embodiment of a system according to the present invention.

DETAILED DESCRIPTION OF THE PREFERRED EMBODIMENTS

Figure 3:
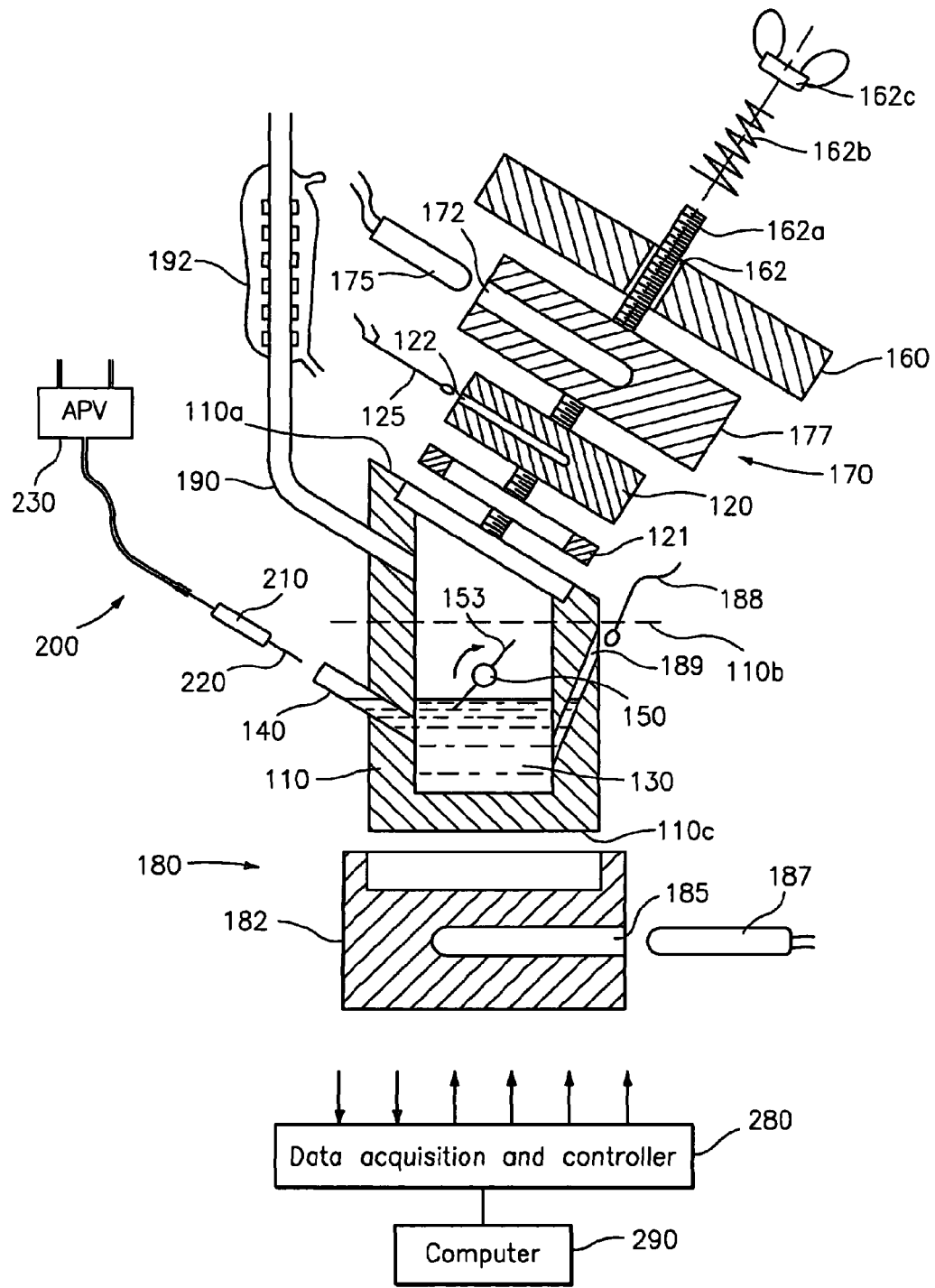
FIG. 3 is a schematic diagram of a side view of one embodiment of a system according to the present invention.

The present invention is directed to a system and method for screening a liquid composition. The liquid composition to be screened may be any substance that is liquid at the operating temperature of the reservoir, and has a sufficiently low enough viscosity to allow the liquid from the reservoir to be applied as a substantially uniform coating on at least a portion of the surface of the test panel. Representative examples of liquid compositions include lubricating oil compositions, fuels, such as gasoline or diesel fuel; aqueous solutions; and polymers and polymer solutions and the like. The preferred liquid composition is a lubricating oil composition. As one skilled in the art would readily understand, lubricating oil compositions can reduce friction, and control wear and corrosion when used as a film between solid surfaces moving relative to one another. Lubricating oil compositions include engine oils, such as lubricants used in the crankcases of engines, and functional fluids such as transmission fluids, hydraulic fluids, gear oils, and the like. Lubricating oil compositions also include greases.

Generally, the lubricating oil composition includes at least an oil of lubricating viscosity, also referred to as a base oil. The expression "base oil" as used herein shall be understood to mean a base stock or blend of base stocks which is a lubricant component that is produced by a single manufacturer to the same specifications (independent of feed source or manufacturer's location); that meets the same manufacturer's specification; and that is identified by a unique formula, product identification number, or both. The base oil for use herein can be any presently known or later-discovered base oil of lubricating viscosity used in formulating lubricating oil compositions for any and all such applications, e.g., engine oils, marine cylinder oils, functional fluids such as hydraulic oils, gear oils, transmission fluids, etc. Additionally, the base oils for use herein can optionally contain viscosity index improvers, e.g., polymeric alkylmethacrylates; olefinic copolymers, e.g., an ethylene-propylene copolymer or a styrene-butadiene copolymer; and the like and mixtures thereof.

As one skilled in the art would readily appreciate, the viscosity of the base oil is dependent upon the application. Accordingly, the viscosity of a base oil for use herein will ordinarily range from about 2 to about 2000 centistokes (cSt) at 100° Centigrade (C.). Generally, individually the base oils used as engine oils will have a kinematic viscosity range at 100° C. of about 2 cSt to about 30 cSt, preferably about 3 cSt to about 16 cSt, and most preferably about 4 cSt to about 12 cSt and will be selected or blended depending on the desired end use and the additives in the finished oil to give the desired grade of engine oil, e.g., a lubricating oil composition having an SAE Viscosity Grade of 0W, 0W-20, 0W-30, 0W-40, 0W-50, 0W-60, 5W, 5W-20, 5W-30, 5W-40, 5W-50, 5W-60, 10W, 10W-20, 10W-30, 10W-40, 10W-50, 15W, 15W-20, 15W-30 or 15W-40. Oils used as gear oils can have viscosities ranging from about 2 cSt to about 2000 cSt at 100° C.

Base stocks may be manufactured using a variety of different processes including, but not limited to, distillation, solvent refining, hydrogen processing, oligomerization, esterification, and rerefining. Rerefined stock shall be substantially free from materials introduced through manufacturing, contamination, or previous use. The base oil of the lubricating oil compositions of this invention may be any natural or synthetic lubricating base oil. Suitable hydrocarbon synthetic oils include, but are not limited to, oils prepared from the polymerization of ethylene or from the polymerization of 1-olefins to provide polymers such as polyalphaolefin or PAO oils, or from hydrocarbon synthesis procedures using carbon monoxide and hydrogen gases such as in a Fischer-Tropsch process. For example, a suitable base oil is one that comprises little, if any, heavy fraction; e.g., little, if any, lube oil fraction of viscosity 20 cSt or higher at 100° C.

The base oil may be derived from natural lubricating oils, synthetic lubricating oils or mixtures thereof. Suitable base oil includes base stocks obtained by isomerization of synthetic wax and slack wax, as well as hydrocracked base stocks produced by hydrocracking (rather than solvent extracting) the aromatic and polar components of the crude. Suitable base oils include those in all API categories I, II, III, IV and V as defined in API Publication 1509, 14th Edition, Addendum I, December 1998. Group IV base oils are polyalphaolefins (PAO). Group V base oils include all other base oils not included in Group I, II, III, or IV. Although Group II, III and IV base oils are preferred for use in this invention, these preferred base oils may be prepared by combining one or more of Group I, II, III, IV and V base stocks or base oils.

Useful natural oils include mineral lubricating oils such as, for example, liquid petroleum oils, solvent-treated or acid-treated mineral lubricating oils of the paraffinic, naphthenic or mixed paraffinic-naphthenic types, oils derived from coal or shale, animal oils, vegetable oils (e.g., rapeseed oils, castor oils and lard oil), and the like.

Useful synthetic lubricating oils include, but are not limited to, hydrocarbon oils and halo-substituted hydrocarbon oils such as polymerized and interpolymerized olefins, e.g., polybutylenes, polypropylenes, propylene-isobutylene copolymers, chlorinated polybutylenes, poly(1-hexenes), poly(1-octenes), poly(1-decenes), and the like and mixtures thereof; alkylbenzenes such as dodecylbenzenes, tetradecylbenzenes, dinonylbenzenes, di(2-ethylhexyl)-benzenes, and the like; polyphenyls such as biphenyls, terphenyls, alkylated polyphenyls, and the like; alkylated diphenyl ethers and alkylated diphenyl sulfides and the derivative, analogs and homologs thereof and the like.

Other useful synthetic lubricating oils include, but are not limited to, oils made by polymerizing olefins of less than 5 carbon atoms such as ethylene, propylene, butylenes, isobutene, pentene, and mixtures thereof. Methods of preparing such polymer oils are well known to those skilled in the art.

Additional useful synthetic hydrocarbon oils include liquid polymers of alpha olefins having the proper viscosity. Especially useful synthetic hydrocarbon oils are the hydrogenated liquid oligomers of $C_6$ to $C_{12}$ alpha olefins such as, for example, 1-decene trimer.

Another class of useful synthetic lubricating oils include, but are not limited to, alkylene oxide polymers, i.e., homopolymers, interpolymers, and derivatives thereof where the terminal hydroxyl groups have been modified by, for example, esterification or etherification. These oils are exemplified by the oils prepared through polymerization of ethylene oxide or propylene oxide, the alkyl and phenyl ethers of these polyoxyalkylene polymers (e.g., methyl poly propylene glycol ether having an average molecular weight of 1,000, diphenyl ether of polyethylene glycol having a molecular weight of 500 to 1000, diethyl ether of polypropylene glycol having a molecular weight of 1,000 to 1,500, etc.) or mono- and polycarboxylic esters thereof such as, for example, the acetic esters, mixed $C_3$-$C_8$ fatty acid esters, or the $C_{13}$ oxo acid diester of tetraethylene glycol.

Yet another class of useful synthetic lubricating oils include, but are not limited to, the esters of dicarboxylic acids e.g., phthalic acid, succinic acid, alkyl succinic acids, alkenyl succinic acids, maleic acid, azelaic acid, suberic acid, sebacic acid, fumaric acid, adipic acid, linoleic acid dimer, malonic acids, alkyl malonic acids, alkenyl malonic acids, etc., with a variety of alcohols, e.g., butyl alcohol, hexyl alcohol, dodecyl alcohol, 2-ethylhexyl alcohol, ethylene glycol, diethylene glycol monoether, propylene glycol, etc. Specific examples of these esters include dibutyl adipate, di(2-ethylhexyl)sebacate, di-n-hexyl fumarate, dioctyl sebacate, diisooctyl azelate, diisodecyl azelate, dioctyl phthalate, didecyl phthalate, dieicosyl sebacate, the 2-ethylhexyl diester of linoleic acid dimer, the complex ester formed by reacting one mole of sebacic acid with two moles of tetraethylene glycol and two moles of 2-ethylhexanoic acid and the like.

Esters useful as synthetic oils also include, but are not limited to, those made from carboxylic acids having from about 5 to about 12 carbon atoms with alcohols, e.g., methanol, ethanol, etc., polyols and polyol ethers such as neopentyl glycol, trimethylol propane, pentaerythritol, dipentaerythritol, tripentaerythritol, and the like.

Silicon-based oils such as, for example, polyalkyl-, polyaryl-, polyalkoxy- or polyaryloxy-siloxane oils and silicate oils, comprise another useful class of synthetic lubricating oils. Specific examples of these include, but are not limited to, tetraethyl silicate, tetra-isopropyl silicate, tetra-(2-ethylhexyl) silicate, tetra-(4-methyl-hexyl)silicate, tetra-(p-tert-butylphenyl)silicate, hexyl-(4-methyl-2-pentoxy)disiloxane, poly(methyl)siloxanes, poly(methylphenyl)siloxanes, and the like. Still yet other useful synthetic lubricating oils include, but are not limited to, liquid esters of phosphorous containing acids, e.g., tricresyl phosphate, trioctyl phosphate, diethyl ester of decane phosphionic acid, etc., polymeric tetrahydrofurans and the like.

The lubricating oil may be derived from unrefined, refined and rerefined oils, either natural, synthetic or mixtures of two or more of any of these of the type disclosed hereinabove. Unrefined oils are those obtained directly from a natural or synthetic source (e.g., coal, shale, or tar sands bitumen) without further purification or treatment. Examples of unrefined oils include, but are not limited to, a shale oil obtained directly from retorting operations, a petroleum oil obtained directly from distillation or an ester oil obtained directly from an esterification process, each of which is then used without further treatment. Refined oils are similar to the unrefined oils except they have been further treated in one or more purification steps to improve one or more properties. These purification techniques are known to those of skill in the art and include, for example, solvent extractions, secondary distillation, acid or base extraction, filtration, percolation, hydrotreating, dewaxing, etc. Rerefined oils are obtained by treating used oils in processes similar to those used to obtain refined oils. Such rerefined oils are also known as reclaimed or reprocessed oils and often are additionally processed by techniques directed to removal of spent additives and oil breakdown products.

Lubricating oil base stocks derived from the hydroisomerization of wax may also be used, either alone or in combination with the aforesaid natural and/or synthetic base stocks. Such wax isomerate oil is produced by the hydroisomerization of natural or synthetic waxes or mixtures thereof over a hydroisomerization catalyst.

Natural waxes are typically the slack waxes recovered by the solvent dewaxing of mineral oils; synthetic waxes are typically the wax produced by the Fischer-Tropsch process.

In one embodiment, a lubricating oil composition includes (a) an oil of lubricating viscosity; and (b) at least one lubricating oil additive. In this embodiment, the oil of lubricating viscosity is typically present in the lubricating oil composition in a major amount, e.g., a major amount of base oil of lubricating viscosity, e.g., an amount of greater than 50 wt. %, preferably greater than about 70 wt. %, more preferably from about 80 to about 99.5 wt. % and most preferably from about 85 to about 98 wt. %, based on the total weight of the composition, and the at least one lubricating oil additive is present in a minor amount. The at least one lubricating oil additive can be any presently known or later-discovered additive used in formulating lubricating oil compositions. The lubricating oil additives for use herein include, but are not limited to, antioxidants, anti-wear agents, detergents such as metal detergents, rust inhibitors, dehazing agents, demulsifying agents, metal deactivating agents, friction modifiers, pour point depressants, antifoaming agents, co-solvents, package compatibilisers, corrosion-inhibitors, ashless dispersants, dyes, extreme pressure agents and the like and mixtures thereof. Greases will require the addition of appropriate thickeners. A variety of the additives are known and commercially available. These additives, or their analogous compounds, can be employed for the preparation of the various lubricating oil compositions herein.

Alternatively, the lubricating oil additive(s) can further contain a diluent oil to form an additive concentrate. These concentrates usually include at least from about 90 wt. % to about 10 wt. % and preferably from about 90 wt. % to about 50 wt. %, of a diluent oil and from about 10 wt. % to about 90 wt. %, preferably from about 10 wt. % to about 50 wt. %, of the foregoing additive(s). Suitable diluents for the concentrates include any inert diluent, preferably an oil of lubricating viscosity such as, for example, a base oil as described hereinabove, so that the concentrate may be readily mixed with lubricating oils to prepare lubricating oil compositions. Suitable lubricating oils that may be used as diluents can be any oil of lubricating viscosity.

Generally the lubricating oil compositions of the present invention will include at least one antioxidant. Antioxidants can reduce the tendency of materials to deteriorate upon exposure to oxygen and heat. Examples of antioxidants include, but are not limited to, hindered phenolic antioxidants, secondary aromatic amine antioxidants, sulfurized phenolic antioxidants, oil-soluble copper compounds, phosphorus-containing antioxidants, organic sulfides, disulfides and polysulfides and the like. The antioxidants will ordinarily be present in the lubricating oil compositions of the present invention at a concentration ranging from about 0.1 to about 5 weight percent.

Representative examples of sterically hindered phenolic antioxidants include, but are not limited to, ortho-alkylated phenolic compounds such as 2,6-di-tertbutylphenol, 4-methyl-2,6-di-tertbutylphenol, 2,4,6-tri-tertbutylphenol, 2-tert-butylphenol, 2,6-diisopropylphenol, 2-methyl-6-tert-butylphenol, 2,4-dimethyl-6-tert-butylphenol, 4-(N,N-dimethylaminomethyl)-2,6-di-tertbutyl phenol, 4-ethyl-2,6-di-tertbutylphenol, 2-methyl-6-styrylphenol, 2,6-distyryl-4-nonylphenol, and their analogs and homologs. Mixtures of two or more such mononuclear phenolic compounds are also suitable.

Representative examples of other phenol antioxidants for use in the lubricating oil compositions of the present invention include, but are not limited to, methylene-one or more of bridged alkylphenols, one or more sterically-hindered unbridged phenolic compounds and mixtures thereof. Examples of methylene-bridged compounds include, but are not limited to, 4,4'-methylenebis(6-tert-butyl o-cresol), 4,4'-methylenebis(2-tert-amyl-o-cresol), 2,2'-methylenebis(4-methyl-6-tert-butylphenol), 4,4'-methylene-bis(2,6-di-tert-butylphenol), and the like. Particularly preferred are mixtures of methylene-bridged alkylphenols such as those described in U.S. Pat. No. 3,211,652, the contents of which are incorporated by reference herein.

Amine antioxidants can also be used in the lubricating oil compositions of this invention. Examples include, but are not limited to, oil-soluble aromatic secondary amines, aromatic secondary polyamines and the like and combinations thereof with aromatic secondary amines being preferred. Examples of aromatic secondary monoamines include diphenylamine, alkyl diphenylamines containing 1 or 2 alkyl substituents each having up to about 16 carbon atoms, phenyl-alpha-naphthylamine, phenyl-beta-napthylamine, alkyl- or aralkyl-substituted phenyl-alpha-naphthylamine containing at least one or two alkyl or aralkyl groups each having up to about 16 carbon atoms, alkyl- or aralkyl-substituted phenyl-beta-naphthylamine containing at least one or two alkyl or aralkyl groups each having up to about 16 carbon atoms, and the like.

A preferred type of aromatic amine antioxidant is an alkylated diphenylamine of the general formula

$$R_1\text{—}C_6\text{—}H_4\text{—}NH\text{—}C_6H_4\text{—}R_2$$

wherein $R_1$ is an alkyl group (preferably a branched alkyl group) having 6 to 12 carbon atoms and preferably 8 or 9 carbon atoms; and $R_2$ is a hydrogen atom or an alkyl group (preferably a branched alkyl group) having 6 to 12 carbon atoms and preferably 8 or 9 carbon atoms. Most preferably, $R_1$ and $R_2$ are the same. One such preferred compound is available commercially as Naugalube® 438L, a material which is understood to be predominately a 4,4'-dinonyldiphenylamine (i.e., bis(4-nonylphenyl)(amine) wherein the nonyl groups are branched.

Another antioxidant for use herein is comprised of one or more liquid, partially sulfurized phenolic compounds such as those prepared by reacting sulfur monochloride with a liquid mixture of phenols wherein at least about 50 weight percent of the mixture of phenols is composed of one or more reactive, hindered phenols and in proportions to provide from about 0.3 to about 0.7 gram atoms of sulfur monochloride per mole of reactive, hindered phenol so as to produce a liquid product. Typical phenol mixtures useful in making such liquid product compositions include a mixture containing by weight about 75% of 2,6-di-tert-butylphenol, about 10% of 2-tert-butylphenol, about 13% of 2,4,6-tri-tertbutylphenol, and about 2% of 2,4-di-tertbutylphenol. The reaction is exothermic and is preferably kept within the range of about 15° C. to about 70° C., most preferably between about 40° C. to about 60° C.

Mixtures of different antioxidants can also be used in the lubricating oil compositions herein. One suitable mixture is comprised of a combination of (i) an oil-soluble mixture of at least three different sterically-hindered tertiary butylated monohydric phenols which is in the liquid state at 25° C., (ii) an oil-soluble mixture of at least three different sterically-hindered tertiary butylated methylene-bridged polyphenols, and (iii) at least one bis(4-alkylphenyl) amine wherein the alkyl group is a branched alkyl group having 8 to 12 carbon atoms, the proportions of (i), (ii) and (iii) on a weight basis falling in the range of about 3.5 to about 5.0 parts of component (i) and about 0.9 to about 1.2 parts of component (ii) per part by weight of component (iii). Examples of such antioxidants discussion above are disclosed in U.S. Pat. No. 5,328,619, the contents of which are incorporated by reference herein. Other useful antioxidants are those disclosed in U.S. Pat. No. 4,031,023, the contents of which are incorporated by reference herein.

Antiwear agents can reduce wear of moving metallic parts in conditions of high loads. Examples of antiwear agents include, but are not limited to, zinc dialkyldithiophosphates and zinc diaryldithiophosphates, e.g., those described in an article by Born et al. entitled "Relationship between Chemical Structure and Effectiveness of Some Metallic Dialkyl- and Diaryl-dithiophosphates in Different Lubricated Mechanisms", appearing in Lubrication Science 4-2 January 1992, see for example pages 97-100; aryl phosphates and phosphites, sulfur-containing esters, phosphosulfur compounds, metal or ash-free dithiocarbamates, xanthates, alkyl sulfides and the like and mixtures thereof.

A detergent can function to neutralize acids that are the product of oxidation, and to suspend insoluble contaminants in a lubricating oil, thereby keeping surfaces contacting the lubricating oil clean, especially high temperature surfaces. Detergents may, for example, contain at least one low number-average molecular weight hydrocarbon group; at least one polar group; and at least one linking group to connect the polar and nonpolar groups. Detergents typically contain metal and are the salts of acids.

Representative examples of detergents include, but are not limited to, overbased or neutral detergents such as sulfonate detergents, e.g., those made from alkyl benzene and fuming sulfuric acid; phenates (high overbased or low overbased), high overbased phenate stearates, phenolates, salicylates, phosphonates, thiophosphonates, ionic surfactants and the like and mixtures thereof. Low overbased metal sulfonates typically have a total base number (TBN) of from about 0 to about 30 and preferably from about 10 to about 25. Low overbased metal sulfonates and neutral metal sulfonates are well known in the art.

Rust inhibitors can protect against the corrosion of ferrous metals. Examples of rust inhibitors include, but are not limited to, nonionic polyoxyalkylene agents, e.g., polyoxyethylene lauryl ether, polyoxyethylene higher alcohol ether, polyoxyethylene nonylphenyl ether, polyoxyethylene octylphenyl ether, polyoxyethylene octyl stearyl ether, polyoxyethylene oleyl ether, polyoxyethylene sorbitol monostearate, polyoxyethylene sorbitol monooleate, and polyethylene glycol monooleate; stearic acid and other fatty acids; dicarboxylic acids; metal soaps; fatty acid amine salts; metal salts of heavy sulfonic acid; partial carboxylic acid ester of polyhydric alcohol; phosphoric esters; (short-chain) alkenyl succinic acids; partial esters thereof and nitrogen-containing derivatives thereof; synthetic alkarylsulfonates, e.g., metal dinonylnaphthalene sulfonates; and the like and mixtures thereof.

Friction modifiers can act to modify the frictional properties of surfaces. Examples of friction modifiers include, but are not limited to, alkoxylated fatty amines; borated fatty epoxides; fatty phosphites, fatty epoxides, fatty amines, borated alkoxylated fatty amines, metal salts of fatty acids, fatty acid amides, glycerol esters, borated glycerol esters; and fatty imidazolines as disclosed in U.S. Pat. No. 6,372,696, the contents of which are incorporated by reference herein; friction modifiers obtained from a reaction product of a $C_4$ to $C_{75}$, preferably a $C_6$ to $C_{24}$, and most preferably a $C_6$ to $C_{20}$, fatty acid ester and a nitrogen-containing compound selected from the group consisting of ammonia, and an alkanolamine, e.g., those disclosed in U.S. Ser. No. 10/402,170, filed Mar. 28, 2003, the contents of which are incorporated by reference herein, and the like and mixtures thereof.

Foam inhibitors can act both to reduce the amount of foam that is formed when a liquid is agitated, and to reduce the time that it takes for the foam to dissipate. Examples of antifoaming agents include, but are not limited to, polymers of alkyl methacrylate; polymers of dimethylsilicone and the like and mixtures thereof.

A dispersant can function to suspend insoluble contaminants in a lubricating oil, thereby keeping surfaces contacting the lubricating oil clean. Dispersants may also function to reduce changes in lubricating oil viscosity by preventing the growth of large contaminant particles in the lubricating oil. Dispersants may, for example, contain at least one high number-average molecular weight hydrocarbon group; at least one polar group; and at least one linking group to connect the polar and nonpolar groups. Dispersants are typically metal-free, generally containing only carbon, hydrogen, nitrogen and oxygen, and sometimes containing boron.

Representative examples of ashless dispersants include, but are not limited to, polyalkylene succinic anhydrides; non-nitrogen containing derivatives of a polyalkylene succinic anhydride; a basic nitrogen compound selected from the group consisting of succinimides, carboxylic acid amides, hydrocarbyl monoamines, hydrocarbyl polyamines, Mannich bases, phosphonoamides, thiophosphonamides and phosphoramides; thiazoles, e.g., 2,5-dimercapto-1,3,4-thiadiazoles, mercaptobenzothiazoles and derivatives thereof; triazoles, e.g., alkyltriazoles and benzotriazoles; copolymers which contain a carboxylate ester with one or more additional polar function, including amine, amide, imine, imide, hydroxyl, carboxyl, and the like, e.g., products prepared by copolymerization of long chain alkyl acrylates or methacrylates with monomers of the above function; and the like and mixtures thereof. The derivatives of these dispersants, e.g., borated dispersants such as borated succinimides, may also be used. Preferably, the dispersants are polyalkylene succinimides derived from animation of polyalkylene succinic anhydrides with polyalkylene polyamine.

In another embodiment, the liquid composition is a fuel composition. Generally, a fuel is a substance used to provide heat and/or power by means of combustion with an oxidant. A fuel composition for use herein includes at least a fuel which can be any presently known or later-discovered fuel used in formulating fuel compositions for any and all such applications and engines, e.g., a wide variety of two stroke and four stroke internal combustion engines such as port fuel injection spark ignition (PFISI) engines, direct injection spark ignition (DISI) engines, diesel, marine, natural gas and hydrogen fueled engines. Accordingly, fuels for use herein include, but are not limited to, motor fuels, e.g., gasoline or diesel which may also contain other components such as alcohols, ethers, or mixture thereof; kerosene; jet fuels; marine bunker fuel; home heating fuel and the like and mixtures thereof For example, when the fuel is diesel, such fuel generally boils above about 212° F. The diesel fuel can comprise atmospheric distillate or vacuum distillate, or a blend in any proportion of straight run and thermally and/or catalytically cracked distillates. Preferred diesel fuels have a cetane number of at least about 40, preferably above about 45, and more preferably above about 50. The diesel fuel can have such cetane numbers prior to the addition of any cetane improver. The cetane number of the fuel can be raised by the addition of a cetane improver.

Also, when the fuel is gasoline, it can be derived from straight-chain naphtha, polymer gasoline, natural gasoline, catalytically cracked or thermally cracked hydrocarbons, catalytically reformed stocks, etc. It will be understood by one skilled in the art that gasoline fuels typically boil in the range of about 80° to about 450° F. and can contain, for example, straight chain or branched chain paraffins, cycloparaffins, olefins, aromatic hydrocarbons, and any mixture of these.

In one embodiment, a fuel composition can include (a) a fuel; and (b) at least one fuel additive. In this embodiment, the fuel is typically present in the fuel composition in a major amount, e.g., an amount of greater than 50 wt. %, preferably greater than about 70 wt. %, more preferably from about 80 to about 99.9 wt. % and most preferably from about 90 to about 99.5 wt. %, based on the total weight of the composition, while the fuel additives are present in the fuel composition in a minor amount.

The fuel additives can be any presently known or later-discovered additive used in formulating fuel compositions. The fuel additives include, but are not limited to, deposit control additives, detergents, cetane improvers, octane improvers, emission reducers, antioxidants, carrier fluids, metal deactivators, lead scavengers, rust inhibitors, bacteriostatic agents, corrosion inhibitors, antistatic additives, drag reducing agents, demulsifiers, dehazers, anti-icing additives, combustion improvers and the like and mixtures thereof. A variety of the additives are known and commercially available. These additives, or their analogous compounds, can be employed for the preparation of the various fuel compositions.

Alternatively, the fuel additive(s) can further contain an inert stable oleophilic organic solvent to form an additive concentrate. These concentrates usually include at least from about 98 wt. % to about 10 wt. %, preferably from about 98 wt. % to about 25 wt. % and most preferably from about 97 wt. % to about 50 wt. % of an inert stable oleophilic organic solvent and from about 2 wt. % to about 90 wt. %, preferably from about 2 wt. % to about 75 wt. % and most preferably from about 3 wt. % to about 50 wt. %, of the foregoing additive(s). Useful inert stable oleophilic organic solvent can be solvents boiling in the range of about 150° F. to about 400° F. Examples of inert solvents include, but are not limited to, aliphatic hydrocarbon solvents, aromatic hydrocarbon solvents, e.g., benzene, toluene, xylene, etc., and the like and mixtures thereof. Aliphatic alcohols containing 3 to about 8 carbon atoms, e.g., isopropanol, n-butanol and the like, in combination with the foregoing hydrocarbon solvents are also suitable for use with the fuel additive.

A deposit control additive can act to clean and/or keep clean entire fuel intake systems. Examples of deposit control additives include, but are not limited to, nitrogen-containing deposit control additives such as, for example, aliphatic hydrocarbyl amines, hydrocarbyl-substituted poly(oxyalkylene) amines, hydrocarbyl-substituted succinimides, Mannich reaction products, nitro and amino aromatic esters of polyalkylphenoxyalkanols, polyalkylphenoxyaminoalkanes and post-treated derivatives of the foregoing nitrogen-containing compounds and the like and mixtures thereof.

Useful aliphatic hydrocarbyl-substituted amines which may be employed in the present invention are typically straight or branched chain hydrocarbyl-substituted amines having at least one basic nitrogen atom and wherein the hydrocarbyl group has a number average molecular weight of about 700 to about 3,000. Preferred aliphatic hydrocarbyl-substituted amines include polyisobutenyl and polyisobutyl monoamines and polyamines. The aliphatic hydrocarbyl amines employed in this invention are prepared by conventional procedures known in the art. Such aliphatic hydrocarbyl amines and their preparations are described in detail in U.S. Pat. Nos. 3,438,757; 3,565,804; 3,574,576; 3,848,056; 3,960,515; 4,832,702; and 6,203,584, the contents of each of which are incorporated by reference herein.

Useful hydrocarbyl-substituted poly(oxyalkylene) amines (also referred to as polyether amines) are generally hydrocarbyl-substituted poly(oxyalkylene) amines, e.g., hydrocarbyl poly(oxyalkylene) monoamines and polyamines wherein the hydrocarbyl group contains from 1 to about 30 carbon atoms, the number of oxyalkylene units range from about 5 to about 100, and the amine moiety is derived from ammonia, a primary alkyl or secondary dialkyl monoamine, or a polyamine having a terminal amino nitrogen atom. Preferably, the oxyalkylene moiety will be oxypropylene or oxybutylene or a mixture thereof. Such hydrocarbyl-substituted poly(oxyalkylene) amines are described, for example, in U.S. Pat. Nos. 5,112,364 and 6,217,624, the contents of which are incorporated by reference herein. A preferred type of hydrocarbyl-substituted poly(oxyalkylene) monoamine is an alkylphenyl poly(oxyalkylene)monoamine wherein the poly(oxyalkylene) moiety contains oxypropylene units or oxybutylene units or mixtures of oxypropylene and oxybutylene units.

An additional type of hydrocarbyl-substituted poly(oxyalkylene)amine are hydrocarbyl-substituted poly(oxyalkylene) aminocarbamates as disclosed, for example, in U.S. Pat. Nos. 4,160,648; 4,191,537; 4,197,409; 4,233,168; 4,236,020; 4,243,798; 4,270,930; 4,288,612 and 4,881,945, the contents of each of which are incorporated by reference herein. These hydrocarbyl poly(oxyalkylene)aminocarbamates contain at least one basic nitrogen atom and have an average molecular weight of about 500 to about 10,000, preferably about 500 to about 5,000, and more preferably about 1,000 to about 3,000. A preferred aminocarbamate is alkylphenyl poly(oxybutylene) aminocarbamate wherein the amine moiety is derived from ethylene diamine or diethylene triamine.

Useful hydrocarbyl-substituted succinimides are generally hydrocarbyl-substituted succinimides, e.g., polyalkyl and polyalkenyl succinimides wherein the polyalkyl or polyalkenyl group has an average molecular weight of about 500 to about 5,000, and preferably about 700 to about 3,000. The hydrocarbyl-substituted succinimides are typically prepared by reacting a hydrocarbyl-substituted succinic anhydride with an amine or polyamine having at least one reactive hydrogen bonded to an amine nitrogen atom. Preferred hydrocarbyl-substituted succinimides include polyisobutenyl and polyisobutanyl succinimides, and derivatives thereof. Examples of hydrocarbyl-substituted succinimides are described, for example, in U.S. Pat. Nos. 5,393,309; 5,588,973; 5,620,486; 5,916,825; 5,954,843; 5,993,497; and 6,114,542, and British Patent No. 1,486,144, the contents of each of which are incorporated by reference herein.

Useful Mannich reaction products are generally obtained from the Mannich condensation of a high molecular weight alkyl-substituted hydroxyaromatic compound, an amine containing at least one reactive hydrogen, and an aldehyde. The high molecular weight alkyl-substituted hydroxyaromatic compounds are preferably polyalkylphenols, e.g., polypropylphenol and polybutylphenol, wherein the polyalkyl group has an average molecular weight of about 600 to about 3,000. The amine reactant is typically a polyamine, such as alkylene polyamines, especially ethylene or polyethylene polyamines, for example, ethylene diamine, diethylene triamine, triethylene tetramine, and the like. The aldehyde reactant is generally an aliphatic aldehyde, such as formaldehyde, including paraformaldehyde and formalin, and acetaldehyde. A preferred Mannich reaction product is obtained by condensing a polyisobutylphenol with formaldehyde and diethylene triamine, wherein the polyisobutyl group has an average molecular weight of about 1,000. Examples of Mannich reaction products are described, for example, in U.S. Pat. Nos. 4,231,759 and 5,697,988, the contents of each of which are incorporated by reference herein.

Additional examples of the foregoing additives are described, for example, in U.S. Pat. Nos. 6,203,584; 6,616,776; 6,651,604 and 6,652,667, the contents of each of which are incorporated by reference herein.

Examples of antioxidants include, but are not limited to, aminic types, e.g., diphenylamine, phenyl-alpha-napthylamine, N,N-di(alkylphenyl) amines; and alkylated phenylene-diamines; phenolics such as, for example, BHT, sterically hindered alkyl phenols such as 2,6-di-tert-butylphenol, 2,6-di-tert-butyl-p-cresol and 2,6-di-tert-butyl-4-(2-octyl-3-propanoic)phenol and the like and mixtures thereof.

Examples of rust inhibitors include, but are not limited to, nonionic polyoxyalkylene agents, e.g., polyoxyethylene lauryl ether, polyoxyethylene higher alcohol ether, polyoxyethylene nonylphenyl ether, polyoxyethylene octylphenyl ether, polyoxyethylene octyl stearyl ether, polyoxyethylene oleyl ether, polyoxyethylene sorbitol monostearate, polyoxyethylene sorbitol monooleate, and polyethylene glycol monooleate; stearic acid and other fatty acids; dicarboxylic acids; fatty acid amine salts; partial carboxylic acid ester of polyhydric alcohol; (short-chain) alkenyl succinic acids; partial esters thereof and nitrogen-containing derivatives thereof and the like and mixtures thereof.

Examples of friction modifiers include, but are not limited to, alkoxylated fatty amines; borated fatty epoxides; fatty phosphites, fatty epoxides, fatty amines, borated alkoxylated fatty amines, metal salts of fatty acids, fatty acid amides, glycerol esters, borated glycerol esters; and fatty imidazolines as disclosed in U.S. Pat. No. 6,372,696, the contents of which are incorporated by reference herein; friction modifiers obtained from a reaction product of a $C_4$ to $C_{75}$, preferably a $C_6$ to $C_{24}$, and most preferably a $C_6$ to $C_{20}$, fatty acid ester and a nitrogen-containing compound selected from the group consisting of ammonia, and an alkanolamine, e.g., those disclosed in U.S. Pat. No. 4,729,769 and U.S. Ser. No. 10/402,170, filed Mar. 28, 2003, the contents of which are incorporated by reference herein, and the like and mixtures thereof.

Examples of antifoaming agents include, but are not limited to, polymers of alkyl methacrylate; polymers of dimethylsilicone and the like and mixtures thereof.

Examples of dispersants include, but are not limited to, polyalkylene succinic anhydrides; non-nitrogen containing derivatives of a polyalkylene succinic anhydride; a basic nitrogen compound selected from the group consisting of succinimides, carboxylic acid amides, hydrocarbyl monoamines, hydrocarbyl polyamines, Mannich bases, copolymers which contain a carboxylate ester with one or more additional polar function, including amine, amide, imine, imide, hydroxyl, carboxyl, and the like, e.g., products prepared by copolymerization of long chain alkyl acrylates or methacrylates with monomers of the above function; and the like and mixtures thereof. The derivatives of these dispersants may also be used. Preferably, the dispersants are polyalkylene succinimides derived from animation of polyalkylene succinic anhydrides with polyalkylene polyamine.

Referring now to FIGS. 1-7, an example of a system for screening a liquid composition is generally illustrated as system 100. Generally, system 100 includes a test cell 110 having a top portion 110a and bottom portion 110c. Test cell 110 includes (i) a test panel 120 removably mounted to the top portion 110a of test cell 110 at an angle to the horizontal 110b of test cell 110; (ii) a reservoir 130 for holding the liquid composition; and (iii) a means 150 for applying a substantially uniform coating of the liquid composition from reservoir 130 to at least a portion of one surface of test panel 120. Test cell 110 can be made of any material which is capable of being stable under testing conditions, e.g., a material resistant to repeated heating to a temperature of about 300° C. under testing conditions. Useful materials include glass, special plastics, metals, etc. In one preferred embodiment, the material for test cell 110 is metal, and more preferably aluminum or an aluminum alloy, such as AU4G.

Test panel 120 is removably mounted to top portion 110a of test cell 110 at an angle to the horizontal 110b of test cell 110 (FIG. 3), which is capable of allowing the liquid composition, when applied to the test panel during testing, to run off the test panel without leaving any drips on the panel. In general, test panel 120 is removably mounted to the top portion of the test cell an angle of between about 10 to about 45 degrees to the horizontal 110b of test cell 110. In one embodiment, the mounting angle is between about 10 to about 30 degrees. In another embodiment, the mounting angle is between about 10 to about 20 degrees. In another embodiment, the mounting angle is about 15 degrees. In one preferred embodiment, the top portion 110a of test cell 110 is constructed so as to be slanted at an angle of between 10 and 45 degrees to the horizontal of test cell 110. This allows for a relatively quick and easy mounting of the test panel onto the test cell.

Test panel 120 will have at least one flat side that is sufficiently large enough to cover the opening of reservoir 130 on the top portion 110a of test cell 110. For the sake of convenience, it is desirable for the length and height of test panel 120 to be smaller than those of test cell 110. In one embodiment it is desirable for test panel 120 to be thick enough to have sufficient thermal mass so as not to vary greatly in temperature. In another embodiment, if it is desired to quickly change the temperature of the test panel during operation, a thin panel can be used. One skilled in the art will be able to readily determine the desired thickness of the test panel. In another embodiment, test panel 120 can include a receptacle 122 for receiving a temperature measuring means 125 such as, for example, a thermocouple.

Test panel 120 can be made of any material which is capable of being stable under test conditions, e.g., a material resistant to repeated heating to a temperature of about 300° C. under test conditions. Suitable materials include metal, plastic or glass material, which may be coated or uncoated over some or all of its surface that is to contact the samples. A preferred material for test panel 120 is aluminum or an aluminum alloy, such as AU4G.

Test panel 120 is removably mounted to top portion 110a of test cell 110 by any means that is secure enough to prevent the lubricating oil composition from leaking from the test panel to outside of the test cell during operation. In one embodiment, top portion 110a of test cell 120 possesses a recess which is adapted to hold test panel 120. If desired, a gasket 121, made out of a material able to withstand prolonged high temperatures such as GORE-TEX®, may be placed in between the reservoir and test panel. In one embodiment, test panel 120 may be mounted onto test cell 110 by, for example, a cover plate 160 drilled with holes 162 and 163 to accommodate bolts 162a and 163a, as shown in FIGS. 2 and 3, is bolted onto the test cell 110 over the top portion 110a with, for example, nut 162c. A constant pressure can be applied onto test panel 120 by using a spring 162b on bolt 162a (see FIG. 3). This is useful to accommodate an expansion of all the various pieces of the system during heating.

Reservoir 130 of test cell 110 contains the liquid composition to be tested. As one skilled in the art will readily appreciate, there is no particular upper limit to the size of the reservoir; however, the reservoir must be large enough to accommodate a headspace above the liquid composition to be tested as well as to accommodate the means for applying the liquid composition from the reservoir across the test panel, and the means for introducing gas. In general, a convenient size for the reservoir is one that can hold a volume of between about 5 and 200 ml, preferably between about 10 and 100 ml, and most preferably between about 20 and 50 ml of the liquid composition.

Figure 4:
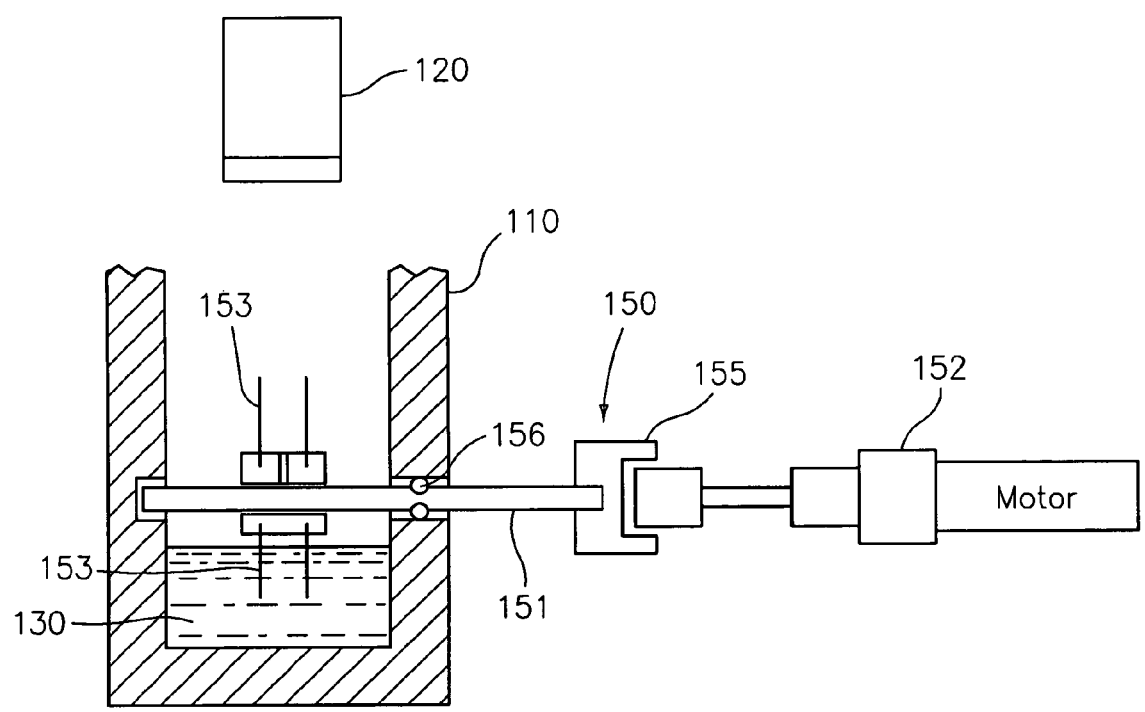
FIG. 4 is a schematic diagram of a side view of one embodiment of a means for applying a substantially uniform coating of a liquid composition to at least a portion of the test panel.

Test cell 110 further includes a means 150 for applying a substantially uniform coating of the liquid composition from reservoir 130 to at least a portion of the surface of test panel 120. For example, as shown in FIG. 4, means 150 for applying a substantially uniform coating of the liquid composition from reservoir 130 to at least a portion of the surface of test panel 120 includes a cylinder 151 mounted inside reservoir 130 on an axle that extends through the walls of test cell 110. The axle can be attached via a coupling system 155 to controlled motor 152 that can be turned on and off to drive the cylinder inside the reservoir. The motor can be controlled by a data acquisition device and controller 280 through computer 290, commonly a personal computer. In use, cylinder 151 has brushes or rods 153 placed on the side of the cylinder to facilitate delivery of the test liquid composition onto the test panel. Seal 156 such as a Viton seal on the axle can be used to prevent any leaks of the liquid composition from the reservoir. The liquid composition can be applied onto test panel 120 according to a controlled program. For example, the means for applying the liquid composition is turned on and applied onto the test panel for a certain time period (i.e., the "soak" period), then the means is turned off for a certain time period (i.e., the "drain" period), thus allowing for a periodic application of the liquid onto the test panel.

System 100 further includes means for heating test panel 120 to a temperature controlled according to a temperature program. Various means for heating test panel 120 are known. For example, heating means 170 can include a receptacle 172 for receiving a resistance heater 175 inserted into a heating block 177 which contacts the test panel when the test panel is mounted onto the test cell. Generally, heating means 170 is mounted over test panel 120 and under cover plate 160. Also, heating means 170 should be of sufficient length so as to cover and be able to heat substantially the entire surface of test panel 120. The means for heating the test panel is according to a controlled temperature program and further includes a means for measuring the temperature of the test panel. This is accomplished by, e.g., a thermocouple inserted into a receptacle in the test panel as discussed above. Both the means for measuring the temperature and means for heating the test panel can be operatively attached to a data acquisition device and controller 280. The computer controller can be operatively associated with a computer 290 equipped with analog-to-digital converter and/or on/off switches for controlling heaters and/or motors. For example, the test panel heating means may include a temperature-controller with an on/off algorithm for maintaining and controlling the desired temperature according to a controlled temperature program, a J-thermocouple sensor, and a voltage controller for maintaining low voltage to the heating element. The test panel can be heated to a constant temperature or can be heated to different temperatures depending on the screening method being carried out.

System 100 further includes means for heating reservoir 130 to a temperature controlled according to a temperature program. Various means for heating reservoir 130 are also known. For example, heating means 180 can be a heating block 182 onto which test cell 110 is mounted, e.g., by means of a collar attached to heating block 182 into which a set screw 181 has been inserted. Heating means 180 can include a receptacle 185 for receiving, for example, an electrical resistance heater 187 into heating block 182. Heating means 180 should be of sufficient length so as to cover and be able to heat substantially the reservoir 130 of test cell 110. The means for heating the reservoir is according to a controlled temperature program and further includes a means for measuring the temperature of the reservoir. In a preferred embodiment, the means for measuring the temperature of the reservoir will directly measure the temperature of the lubricating oil composition being tested, i.e., the bulk. This may be accomplished by, for example, insertion of a temperature measuring means 188 such as a thermocouple through at least one inlet 189 to directly contact the lubricating oil composition. Both the means for measuring the temperature of the reservoir and means for heating the reservoir can be operatively attached to data acquisition device and controller 280. The computer controller can be operatively associated with computer 290 equipped with analog-to-digital converter and/or on/off switches for controlling heaters and/or motors. For example, the reservoir heating means may include a temperature-controller with an on/off algorithm for maintaining the temperature, a J-thermocouple sensor, and a voltage controller for maintaining low voltage to cell heating element.

System 100 can further include a means for cooling reservoir 130 of test cell 110. The cooling means can include a plurality of elongated cooling fins 105, 106 and 107 (see FIG. 1.).

System 100 further includes a means for supplying an oxidizing gas to the test cell. The gas means may preferably include an inlet 140 for introducing an oxidizing gas, a gas supply capable of maintaining constant flow, and a flow meter for measuring the flow rate of the oxidizing gas.

In one embodiment, system 100 further includes means 200 for supplying an oxidizing gas and also for measuring the viscosity of the liquid. As shown in FIG. 3, system 100 includes means 200 which includes a manifold 210 and capillary 220 which are introduced through inlet 140 and immersed in the liquid. Means 200 can allow for bubbling of the oxidizing gas in the liquid in the test cell and also for measurement of the viscosity of the liquid composition, i.e., the bulk, in reservoir 130. Various means 200 are known and include, for example, an alternate pressure viscometer such as those disclosed in U.S. Patent Application Publication Nos. 2008/0127717 and US2008/0127718, the contents of which are incorporated by reference herein.

Figure 5:
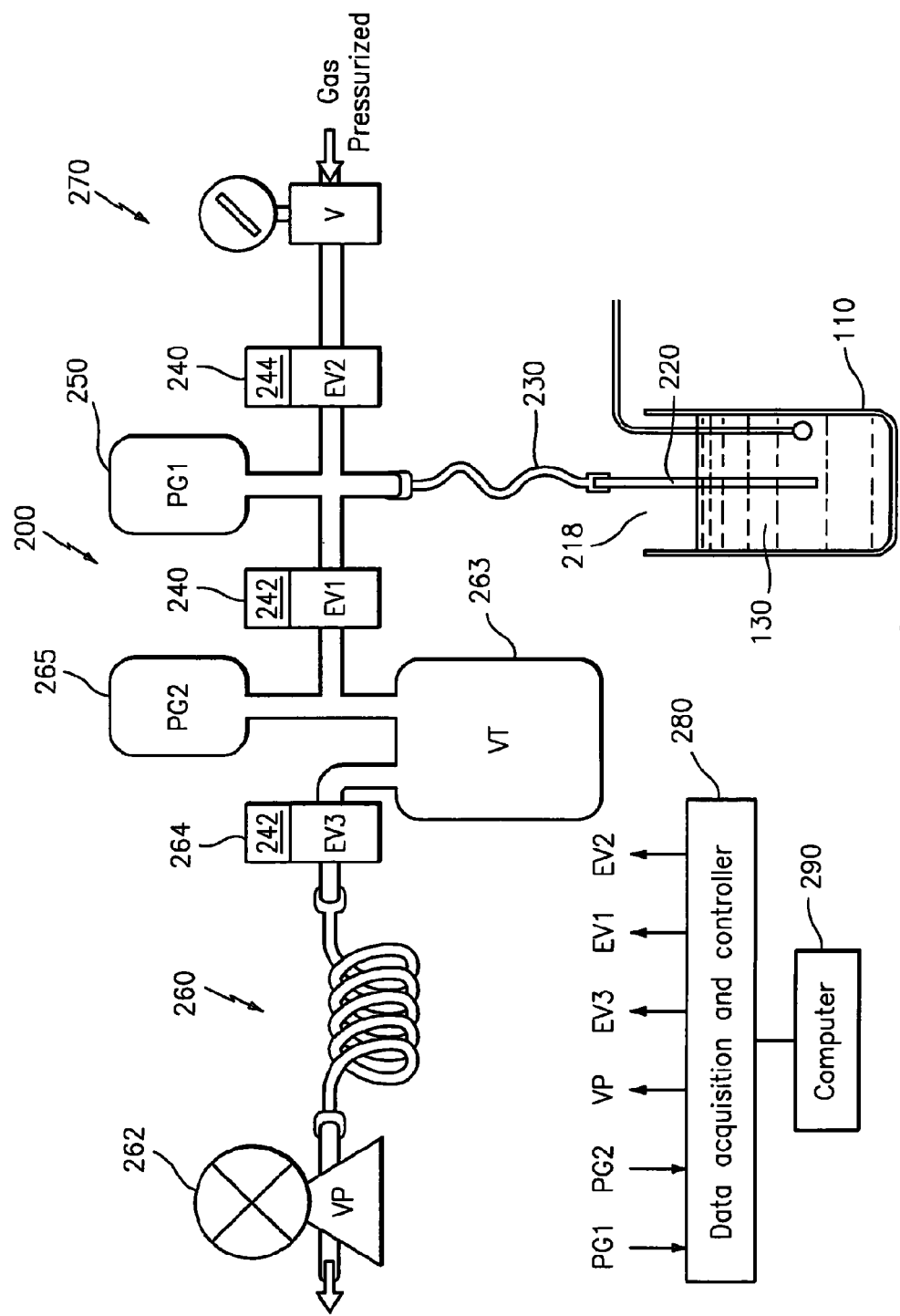
FIG. 5 is a schematic diagram of an exemplary alternate pressure viscometer device.

For example, FIG. 5 shows a schematic plan of a means 200 which can be used for determining a rheological property of a liquid composition. It is particularly suited for determining a change in the flow of the test liquid composition by repeated evaluation of the test liquid over time and thus suitable for use in measuring viscosity as well as changes in viscosity. More specifically, in FIG. 5, the means 200 can be used to determine the dynamic viscosity of a test liquid composition. Means 200 includes a capillary 220 in communication with the test liquid composition contained in reservoir 130. The capillary 220 provides a restriction to flow path and is selected to be a suitable length to mitigate end effects and of a cross section suitable to achieve laminar flow in the region. The capillary 220 is conveniently selected as being a long thin circular tube, commonly a needle. The capillary can also be selected such as to resemble a cylindrical annulus defining an annular region between two coaxial circular cylinders or a narrow slit formed by two narrow walls. Preferably, the capillary is a capillary tube.

The capillary 220 is connected by a manifold 210 to a selectable valve 240. The capillary 220 together with manifold 210 and valve 240 define a chamber of a predetermined volume. The volume of the chamber can be determined empirically, calculated, or by other suitable methods. In operation, the chamber receives a portion of the test liquid which flows through capillary 220 under the influence of a difference in pressure across the capillary system. The driving pressure can be positive pressure or vacuum, however it is important that the driving force be reproducible and relatively fast acting onto the chamber.

The chamber is outfitted with a pressure sensor 250 which can be used to record the differential pressure in the chamber during a measurement cycle. The differential pressure can be output for data acquisition and control and to a computing device for recordation and further manipulation. The selectable valve 240 can be a single valve, such as for example a three way valve which conveniently can be in communication with a regulated pressure source 260, a second pressure source 270 and the pressure gauge 250. In one embodiment, the regulated pressure source 260 and the second pressure source 270 are offset by more than one selectable valve 240 such as 242 EV1 which can be a normally closed electrovalve and 244 EV2 which can be a normally open electrovalve, wherein the electrovalves can be controlled by a data acquisition device and controller 280. The electrovalves are selected to be relatively fast acting valves, with valve actuation occurring in fractional seconds.

Pressure sensor device 250 converts said pressure measured to an electrical signal, typically a voltage or current capable or being converted to a digital signal for processing by a data acquisition and controller device 280. Typically, the electrical signal output by the pressure sensor is a direct current voltage, being in the order of several volts. The output signal can also be direct current amperage, measured in milliamps. The pressure sensor can be used to measure differential pressure for example between the chamber and ambient pressure. The data acquisition and controller device 280 is used to convert the electrical signals to digital data for further computation with a computer 290, commonly a personal computer. Typically, the conversion is analog to digital conversion. Modules combining data acquisition device, a control device and a computing device are commercially available.

The regulated pressure source 260 provides the motive force for inducing a test liquid to flow through capillary 220 and into the chamber. The regulated pressure source 260 is discontinuous in a test cycle, it is quickly applied to a predetermined setpoint to create a differential pressure which is dynamic and changes as the test liquid is induced into the chamber. A preferred pressure source is a regulated reduced pressure source 260, such as a vacuum source. Regulation of the vacuum source may be accomplished by numerous methods known in the art.

In one embodiment, the reduced pressure source employs a vacuum pump 262 coupled to a vacuum tank 263 equipped with a vacuum tank pressure gauge 265. The vacuum tank is regulated around a set point by at least one vacuum tank selectable valve 264; typical set points are from −50 millibars to −150 millibars and have a desired precision from about +/−1 millibar around the set point. The vacuum tank pressure gauge 265 measures the vacuum in the vacuum tank 263. When this measure is greater than the desired precision, a controller 280 can open a vacuum tank selectable valve 264 and optionally commence operation of the vacuum pump 262 for a period of time until the vacuum regulation is within the desired precision. In a similar fashion, if the vacuum tank is a pressure lower than the desired precision, a gas can be introduced into the vacuum tank.

A second pressure source 270 is coupled to at least one selectable valve 240 and used to evacuate the test liquid from the capillary 220. The second pressure source is regulated in flow and pressure using suitable techniques. These parameters are not critical and selected under suitable conditions to induce the test sample to evacuate the capillary system and thus are selected with reference to the regulated pressure source 260. Typical parameters are around 0.5 bar (from about 0.1 bar to about 5.0 bar) and around 1.0 liter/hour (from 0.1 liter/hr to about 5 liters/hr).

Second pressure source 270 is an oxidizing gas so that the test liquid can be profiled by viscosity change in reference to oxidation. During operation, the second pressure source flow and pressure can be adjusted to slowly bubble a gas through the test fluid. Second pressure source 270 is integrated into the operation and serves the dual function of evacuating the test sample from the capillary and to serve as an oxidative gas source.

Figure 6:
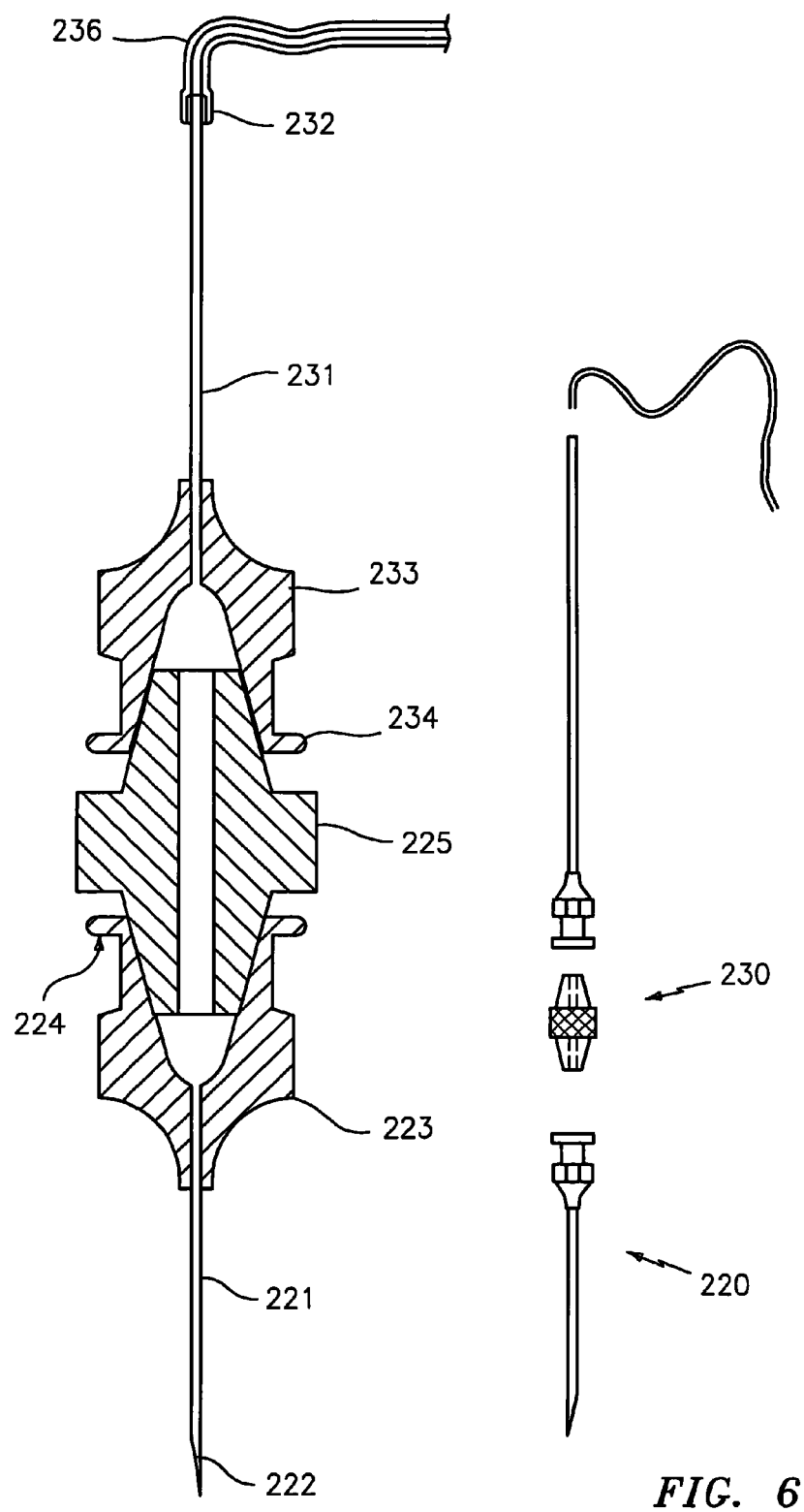
FIG. 6 is a partial exploded view of a capillary comprising a syringe.

FIG. 6 shows a partial exploded view of manifold 210 which includes the capillary 220. The capillary includes a stainless steel hypodermic needle 221 which has a uniform diameter (d) over a predetermined length (l) with l>d. One end of needle 221 has a flat tip 222 which is submersed in the liquid in reservoir 130 during a measurement. The size and length of the needle can be varied according to the expected fluid properties over the measurement. A suitable needle is, for example, a 25 G, 1" long Luer. Common commercial syringe needles presented in gauge size such as Gauge 10 to Gauge 33, with the higher number referring to the smaller nominal inside diameter can be selected. For example, the needle has been selected to have a length of from between about 10 mm to about 100 nun with an inner diameter from bout 0.1 mm to about 1.5 mm. The diameter of the capillary tube is pre-selected in accordance with the test sample.

The opposing end from flat tip 222 has a standard Luer hub 223, which is used to connect capillary 220 to viscometer 210. The Luer hub 223 has a flanged head 224 which communicates with a connector 225 illustrated by a male/male Luer connector. The other end of the connector 225 is attached to a similar needle 231 such as a 20 G, 6" long Luer. The tip end of this is attached to a tube 236 which ultimately attaches to at least one selectable valve, not illustrated. The internal volume for the manifold 210 including the capillary 220 is fixed by the selection of the components having the internal recesses and provides a flow path for the test liquid.

Figure 7:
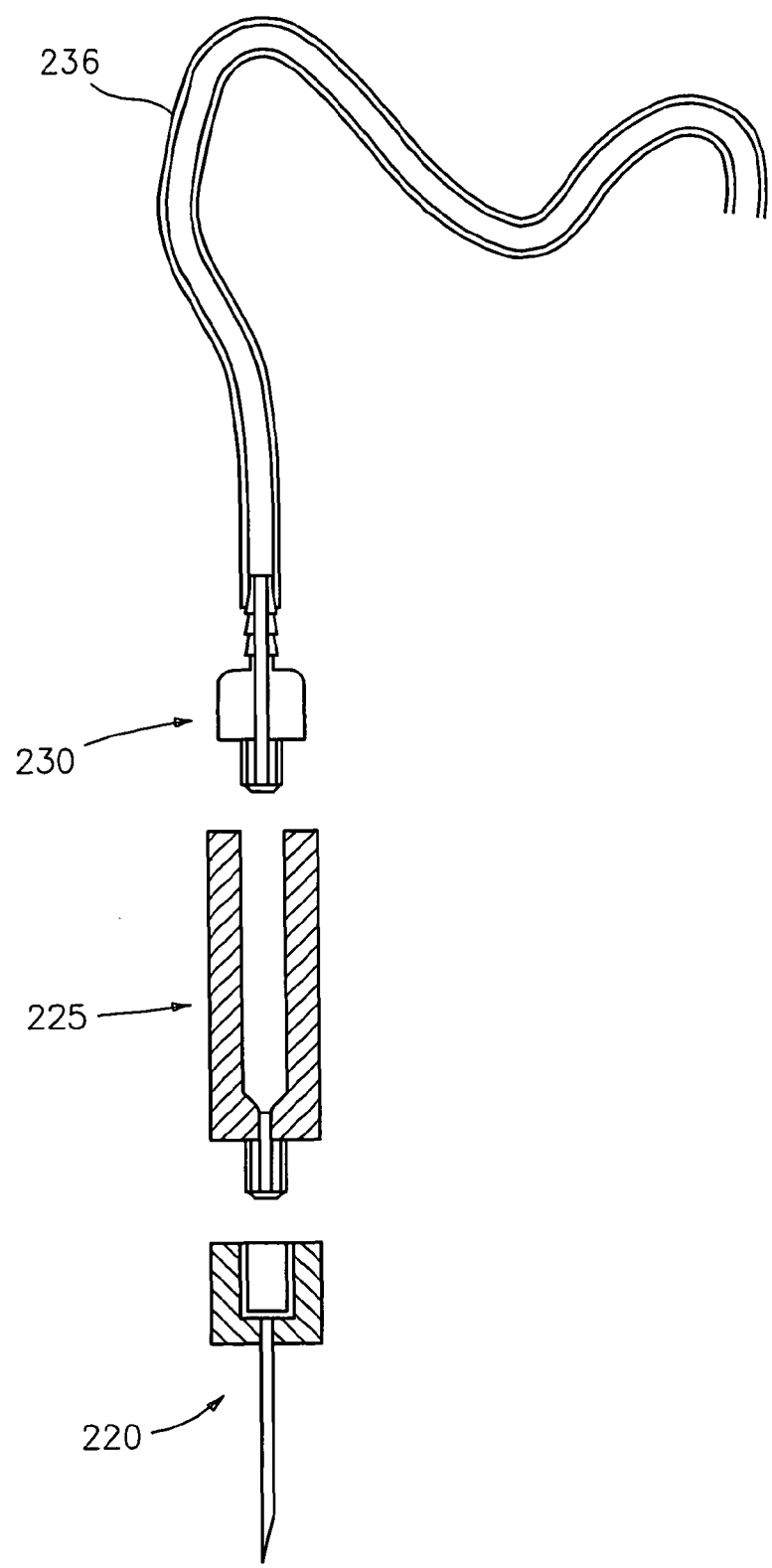
FIG. 7 is a cross sectional view of a capillary with a connector.

FIG. 7 illustrates an alternative capillary and viscometer arrangement indicating alternative connector member configurations. Numerous suitable connectors and fasteners are known in the art, e.g., Luer locks and Luer slip-ons, threaded connectors, connectors to tubing, etc. Connector 225 in FIG. 7 can be fabricated to have a larger internal volume for retaining a larger volume of the test liquid in a measurement cycle. This larger volume may also serve and prevent an aliquot of the test liquid from contaminating non-wetted areas of the viscometer. It is particularly desirable to avoid contamination of sample to the regulated vacuum source. Also, advantageously, the components which define the viscometer are inexpensive and easily replaced. Thus, for example, these components could be a single use or readily disposable if the test liquid plugs and/or contaminates the components. As is common in oxidation tests, the oxidation by-products contaminate the capillary tubes and are not readily cleaned.

In one preferred embodiment, test cell 110 further includes at least one outlet 190 for exhaust gas and any vaporized liquid, and cooling means 192 to return evaporated liquid into reservoir 130 (see FIGS. 1-3). The addition of a cooling means advantageously allows for a reduction in the loss of liquid during the screening method, which can be particularly useful for the analysis of volatile liquids. A preferred cooling means is a condenser.

Generally, a method for screening a liquid composition according to the present invention involves:

(a) providing a test cell having a top portion and a bottom portion, the test cell comprising (i) a test panel removably mounted to a top portion of the test cell at an angle of between about 10 to about 45 degrees to the horizontal of the test cell; (ii) a reservoir for holding the lubricating oil composition; and (iii) a means for applying the liquid composition from the reservoir to the test panel;

(b) introducing the liquid composition into the reservoir of the test cell;

(c) heating the test panel according to a first temperature controlled program;

(d) heating the reservoir according to a second temperature controlled program, wherein the test panel is heated to a temperature greater than the temperature of the reservoir;

(e) introducing an oxidizing gas to the test cell;

(f) applying a substantially uniform coating of the liquid composition from the reservoir to at least a portion of the test panel; and (g) measuring the oxidation stability of the liquid composition.

First, the reservoir is filled with the selected liquid composition. As one skilled in the art will readily understand, in the event that a highly viscous liquid composition is used, the reservoir can be pre-heated to facilitate a lower viscous fluid liquid, i.e., a liquid having a melting point equal to or less than the start-of-cycle temperature of the reservoir, so that the material is liquid during the entire screening method. Once the reservoir is filled, the test panel can be placed on the top of the test cell to close the system.

The reservoir of the test cell will be heated according to a temperature controlled program as discussed hereinabove. In one embodiment, a temperature range for heating the reservoir of the test cell according to a temperature controlled program is in the range of about 130° C. to about 220° C. In another embodiment, the temperature range is about 150° C. to about 200° C. In another embodiment, the temperature range is about 160° C. to about 180° C. In one preferred embodiment, the temperature of about 170° C. can be used. The heating can be started after the sample liquid composition has been introduced into the test cell or the test cell can be preheated and then the sample liquid is introduced therein. Of course, within the safety limits of operation of the system, the temperatures can be varied over a wide range to suit the characteristics of the liquid.

In order to assist in oxidizing the liquid composition, a catalyst may be used. For example, a catalyst can be mixed with the liquid composition before or after the liquid composition is introduced in the test cell. A suitable catalyst includes a metallic oxidation catalyst, e.g., a combination of metal ions such as copper, lead and aluminum.

The test panel will be heated according to a temperature controlled program discussed hereinabove. The temperature of the test panel will be higher than the temperature of the reservoir. In general, the temperature range for heating the test panel is about 250° C. to about 350° C. In one embodiment, the test panel is heated to a temperature ranging from about 275° C. to about 330° C. In one embodiment, the test panel is heated to a temperature ranging from about 280° C. to about 320° C. In one preferred embodiment, a temperature of about 295° C. can be used.

The oxidizing gas may be any gas which is capable of oxidizing the test liquid composition under the oxidation conditions. Generally, any gas containing an effective amount of oxygen can be used. Representative examples of a suitable gas include air, pure oxygen, nitrogen oxides, nitrogen dioxides, sulfur oxides and the like mixtures thereof. The oxidizing gas can also include additional gases, such as noble gases, e.g., argon, neon, and helium. Preferably, air is used as the gas. An advantage of the system and method of the present invention is that since the sample size is much smaller and the test length is relative short, less oxidizing gas needs to be used.

The oxidizing gas may be delivered to the test cell at a constant flow rate. Typical flow rates of the oxidizing gas range from about 0.5 to about 2 1/hour, with about 1 1/hour being preferred The oxidation of the liquid composition in the test cell is performed for a specified time. Although the duration for the oxidation of the liquid is not limited, the duration can range from several hours to several days. In one embodiment, the duration for the oxidation of the liquid can range from about 18 to about 24 hours. The latter time compares favorably with the test duration for typical oxidation and detergency tests, which can take hundreds of hours to complete.

If desired, the liquid can be stirred and/or agitated during the delivering of the gas to the test cell and/or the heating of the liquid in the test cell.

Generally, a substantially uniform coating of the liquid composition is applied to at least a portion of the test panel. By "substantially uniform coating" is meant a relatively contiguous coating of the liquid composition applied on the portion of the test panel which is ordinarily of the same thickness, i.e., a uniform thickness. A substantially uniform coating on the test panel advantageously allows for the test panel, after being subject to an oxidation cycle, to have a generally consistent colored appearance across the entire surface that is exposed to the test reservoir. In this manner, the generally consistent colored appearance of the coating on the test panel can be rated according to any of the standard panel rating to determine the detergency properties of the liquid composition, as discussed hereinbelow. In one preferred embodiment, the liquid composition is applied to the test panel in an intermittent manner, and not in a continuous manner. For example, a substantially uniform coating of the liquid composition can first be applied to the test panel for a cycle of about 5 seconds (i.e., the "soak" period), followed by about 15 seconds of draining of the liquid from the panel (i.e., the "drain" period). In this manner, the formation of a substantially uniform coating or substantially uniform thin film of the liquid composition on the test panel can be achieved thereby simulating the thin film oxidation and detergency behavior of, for example, a lubricating oil composition in addition to its bulk behavior. In this manner, both the surface properties and the bulk properties of the liquid composition can be determined.

For determination of oxidation stability of the liquid composition, the liquid composition is analyzed by the means for determining oxidation stability. Various means for determining oxidation stability are known and generally include viscometric determinations, infrared absorbance, mass spectrometry, measuring the total base or total acid number, and the like. Oxidation stability data results of the test can be converted to an electrical or optical signal and transmitted via a signal transmission line to a computer controller.

In one embodiment, oxidation stability of the liquid composition in the reservoir, i.e., the bulk, is determined by periodically measuring the viscosity of the liquid composition during the oxidation period. The viscosity can be measured by means of an online viscosity measurement apparatus, such as the apparatus and method disclosed in U.S. Patent Application Publication Nos. 2008/0127717 and 2008/0127718 as discussed hereinabove. The viscosity can be measured at any time during the oxidation cycle such as, for example, once every 5 minutes.

In another embodiment, oxidation stability is determined by measuring the infrared absorbance of the liquid periodically during the oxidation period. The degree of oxidation is then determined by measuring the infrared absorbance of the carbonyl peak at 1710 cm$^{-1}$ using, e.g., a Fourier transform infrared spectrometer (e.g. a Bruker IFS 48 infrared apparatus). As oxidation takes place, the absorbance peak at 1710 cm$^{-1}$ increases owing to oxidation of the test liquid as carbonyl-containing functional groups are produced. The data can then be recorded in a database.

In another embodiment, oxidation stability is determined by introducing a fiber optic probe having a proximal end and a distal end for transmitting light energy into the reservoir of the test cell. A light source for generating excitation energy is operatively associated with the optical fiber probe such that said excitation light passes through the optical fiber probe, and a detection means is operatively associated with the optical fiber means for detecting an emission and/or absorption signal generated from the test cell. The test cell will be of a material which is suitable for light adsorption, e.g., borosilicate glass. The data can then be recorded in a database.

In one preferred embodiment, the screening method includes determining the detergency properties of the liquid composition by rating the test panel according to any of the standard panel rating methods after the oxidation cycle has concluded as known in the art. In one embodiment, the test panel can be rated by visually comparing the generally consistent colored appearance of the coating on the test panel to a standard rating chart such as a CEC M-02-A-78 color chart and assigning a numerical value based on the colored appearance, e.g., a rating where a value of 10 is the lightest color and a value of 0 is the darkest color, as known in the art. The rating of the test panel involving a visual comparison with the known rating standard is generally conducted after the test panel has been cleaned and dried. Alternatively, after cleaning and drying, deposits can be removed from the panels and weighed.

EXAMPLES

A closed test cell for oxidative conditions was prepared in accordance with the present invention and four oils were analyzed four times each according to the following parameters:

Test duration: 24 hours
Panel temperature: 295° C.
Reservoir temperature: 170° C.
Gas: air
Gas flow: 1 liter/hour
Sequential projection: Soak time 5 seconds
Drain time 15 seconds
Sample size: 10 ml After the test was complete, the test panel was softly cleaned and the visual appearance of the panel was rated using an automated video rater based on the CEC M-02-A-78 color chart. A rating of 10 is the lightest and 0 is the darkest. The results of this test are set forth below in Table 1

TABLE 1

|  | Oil 1 | Oil 2 | Oil 3 | Oil 4 |
| --- | --- | --- | --- | --- |
| Measurement 1 | 9.8 | 0.2 | 2.5 | 5.0 |
| Measurement 2 | 9.4 | 0.3 | 2.5 | 4.9 |
| Measurement 3 | 9.9 | 1.0 | 2.5 | 5.0 |
| Measurement 4 | 9.7 | 0.8 | 2.7 | 5.1 |
| Mean | 9.70 | 0.57 | 2.55 | 5.00 |
| Standard deviation | 0.2 | 0.4 | 0.1 | 0.1 |

Figure 8:
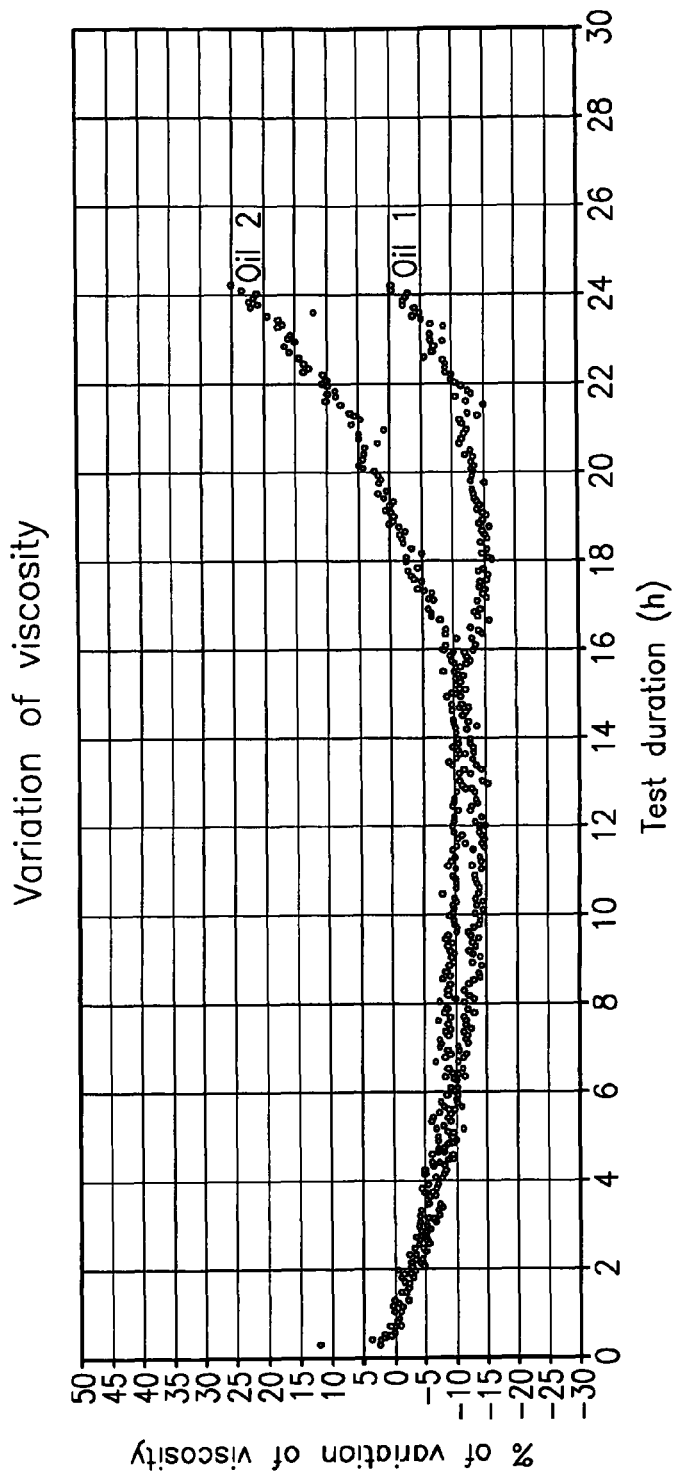
FIG. 8 is a graph showing the time vs. viscosity plots for Oils 1 and 2.

In addition, the viscosity of each test oil was measured during the oxidation cycle. The viscosity variation was measured using the online viscosity measurement apparatus and method as described in U.S. Patent Application Publication Nos. 2008/0127717 and 2008/0127718. The viscosity of each test oil was measured at 5 minute intervals during the oxidation cycle of each test. A graph showing a representative time vs. viscosity plot for test oils 1 and 2 of Table 1 are shown in FIG. 8.

While the above description contains many specifics, these specifics should not be construed as limitations of the invention, but merely as exemplifications of preferred embodiments thereof. Those skilled in the art will envision many other embodiments within the scope and spirit of the invention as defined by the claims appended hereto.

What is claimed is:

1. A system for screening a liquid composition, the system comprising:
   (a) a test cell having a top portion and a bottom portion, the test cell comprising (i) a test panel removably mounted to the top portion of the test cell at an angle of between about 10 to about 45 degrees to the horizontal of the test cell; (ii) a reservoir for holding the liquid composition; and (iii) a means for applying a substantially uniform coating of the liquid composition from the reservoir to at least a portion of the test panel;
   (b) a means for heating the test panel according to a first temperature control program;
   (c) a means for heating the reservoir according to a second temperature control program; and
   (d) a means for supplying an oxidizing gas to the test cell;
   wherein the means for supplying the oxidizing gas comprises an apparatus for determining a rheological property of the liquid composition, the apparatus comprising a capillary having a first end and a second end with a substantially uniform diameter over a predetermined length; the first end disposed for fluid communication with the liquid composition to be measured, the second end attached to a manifold having at least one selectable valve, the capillary together with the manifold and the at least one selectable valve define a chamber of predetermined volume, a regulated pressure source initially applied to induce the sample into the capillary and generate a differential pressure in the chamber, a pressure sensor attached to the chamber for outputting differential pressure to a computing device, and a second pressure source coupled to the at least one selectable valve for evacuating the sample from the capillary and supplying the oxidizing gas to the reservoir.

2. The system of claim 1, wherein the liquid composition is a lubricating oil composition.

3. The system of claim 2, wherein the lubricating oil composition comprises an oil of lubricating viscosity.

4. The system of claim 2, wherein the lubricating oil composition comprises a major amount of an oil of lubricating viscosity; and a minor amount of at least one lubricating oil additive.

5. The system claim 1, wherein the liquid composition is a fuel composition.

6. The system of claim 5, wherein the lubricating oil composition comprises a major amount of a fuel; and a minor amount of at least one fuel additive.

7. The system of claim 1, wherein the means for applying the liquid composition comprises an axle having brushes thereon and a motor operatively connected thereto.

8. The system of claim 1, wherein the means for heating the test panel comprises a heating element mounted on the test panel.

9. The system of claim 1, wherein the means for heating the reservoir comprises a heating element mounted on the bottom portion of the test cell.

10. The system of claim 1, wherein the means for heating the test panel comprises a temperature-controller with an on/off algorithm for maintaining the temperature, and a thermocouple sensor.

11. The system of claim 1, wherein the means for heating the reservoir comprises a temperature-controller with an on/off algorithm for maintaining the temperature, and a thermocouple sensor.

12. The system of claim 1, wherein the means for supplying the oxidizing gas comprises an oxidizing gas supply capable of maintaining constant flow, and a flow meter for measuring the flow rate of the oxidizing gas.

13. The system of claim 1, further comprising an effluent oxidizing gas outlet.

14. The system of claim 13, wherein the effluent gas outlet is in fluid communication with a condenser.

15. The system of claim 1, further comprising a means for measuring the oxidation stability of the liquid composition.

16. The system of claim 1, further comprising a controller coupled to the system.

17. A method for screening a liquid composition, the method comprising:
   (a) providing a test cell having a top portion and a bottom portion, the test cell comprising (i) a test panel removably mounted to a top portion of the test cell at an angle of between about 10 to about 45 degrees to the horizontal of the test cell; (ii) a reservoir for holding the lubricating oil composition; and (iii) a means for applying the liquid composition from the reservoir to the test panel;
   (b) introducing the liquid composition into the reservoir of the test cell;
   (c) heating the test panel according to a first temperature controlled program;
   (d) heating the reservoir according to a second temperature controlled program, wherein the test panel is heated to a temperature greater than the temperature of the reservoir
   (e) introducing an oxidizing gas to the test cell;
   (f) applying a substantially uniform coating of the liquid composition from the reservoir to at least a portion of the test panel; and
   (g) measuring the oxidation stability of the liquid composition,
   wherein measuring the oxidation stability of the liquid composition comprises determining a rheological property of the liquid composition by the step comprising:
      (i) placing a capillary in fluid communication with the fluid sample, wherein the capillary has a first end and a second end with a substantially uniform diameter over a predetermined length, the first end being submerged in the fluid sample to be measured, the second end attached to a manifold having at least one selectable valve, the capillary together with the manifold and the at least one selectable valve define a chamber of predetermined volume;
      (ii) actuating at least one selectable valve attached to the manifold to allow a gas to enter into and pass through the manifold and capillary;
      (iii) inducing the sample into the capillary by rapidly generating a dynamic differential pressure in the chamber thus allowing the sample to flow from the reservoir through the capillary;
      (iv) detecting pressure change of the chamber as a result of the fluid flow; and
      (v) relating the rate of pressure change to a rheological property.

18. The method of claim 17, wherein the liquid composition is a lubricating oil composition.

19. The method of claim 18, wherein the lubricating oil composition comprises an oil of lubricating viscosity.

20. The method of claim 18, wherein the lubricating oil composition comprises a major amount of an oil of lubricating viscosity; and a minor amount of at least one lubricating oil additive.

21. The method of claim 17, wherein the liquid composition is a fuel composition.

22. The method of claim 21, wherein the lubricating oil composition comprises a major amount of a fuel; and a minor amount of at least one fuel additive.

23. The method of claim 17, wherein the oxidizing gas is introduced to the test cell at a constant flow rate through the test cell.

24. The method of claim 17, wherein the test panel is heated to a temperature ranging from about 280° C to about 320° C and the reservoir is heated to a temperature ranging from about 160° C to about 180° C.

25. The method of claim 17, wherein the liquid composition is applied intermittently to the test panel.

26. The method of claim 17, wherein the step of measuring the oxidation stability of the liquid composition further comprises using infrared spectroscopy.

27. The method of claim 17, wherein the step of measuring the oxidation stability of the liquid composition comprises measuring the viscosity of the liquid composition.

28. The method of claim 17, wherein the measured oxidation stability of the liquid composition obtained in step (g) is outputted and stored on a data carrier.

29. The method of claim 17, further comprising determining the detergency of the liquid composition.

* * * * *